(12) United States Patent
Schoenhaus

(10) Patent No.: US 9,380,827 B1
(45) Date of Patent: Jul. 5, 2016

(54) POST-OPERATIVE SHOE AND METHOD FOR CONSTRUCTION THEREOF

(71) Applicant: Propet Global Limited, Auburn, WA (US)

(72) Inventor: Harold D. Schoenhaus, Del Ray Beach, FL (US)

(73) Assignee: PROPET GLOBAL LIMITED, Auburn, WA (US)

( * ) Notice: Subject to any disclaimer, the term of this patent is extended or adjusted under 35 U.S.C. 154(b) by 271 days.

(21) Appl. No.: 13/896,277

(22) Filed: May 16, 2013

(51) Int. Cl.
| A61F 5/14 | (2006.01) |
| A43B 7/00 | (2006.01) |
| A61F 5/01 | (2006.01) |
| A43B 13/12 | (2006.01) |
| A43B 7/14 | (2006.01) |

(52) U.S. Cl.
CPC . *A43B 7/00* (2013.01); *A43B 7/147* (2013.01); *A43B 13/122* (2013.01); *A61F 5/0195* (2013.01)

(58) Field of Classification Search
CPC ............ A43B 7/00; A43B 7/147; A43B 9/00; A43B 13/12; A43B 13/122
USPC .................. 36/25 R, 150, 156, 157, 178, 181
See application file for complete search history.

(56) References Cited

U.S. PATENT DOCUMENTS

| 2,599,740 | A | * | 6/1952 | Beveridge | A43B 3/128 36/11.5 |
| 4,430,810 | A | * | 2/1984 | Bente | A43B 13/14 36/136 |
| 4,773,170 | A | * | 9/1988 | Moore | A61F 5/0195 36/11.5 |
| 5,176,624 | A | * | 1/1993 | Kuehnreich | A43B 3/26 2/22 |
| 5,797,862 | A | * | 8/1998 | Lamont | A43B 5/0415 36/154 |
| 6,006,451 | A | * | 12/1999 | Morris | A43B 1/0027 36/107 |
| 6,115,946 | A | * | 9/2000 | Morris | A43B 1/0027 36/107 |
| 6,282,818 | B1 | * | 9/2001 | Lu | A43B 3/24 36/100 |
| 7,146,751 | B2 | * | 12/2006 | Seamans | A43B 1/0081 36/11.5 |
| 8,458,930 | B2 | * | 6/2013 | Ha | A43B 7/142 36/150 |
| 2004/0118019 | A1 | * | 6/2004 | Ito | A43B 1/0027 36/50.1 |
| 2004/0211091 | A1 | * | 10/2004 | Heierling | A43B 5/04 36/117.1 |
| 2008/0256828 | A1 | * | 10/2008 | Doran | A43B 1/0027 36/88 |
| 2009/0107010 | A1 | * | 4/2009 | Rutherford | A43B 5/00 36/132 |
| 2010/0275460 | A1 | * | 11/2010 | Ha | A43B 7/142 36/28 |
| 2011/0023335 | A1 | * | 2/2011 | Carol | A43B 3/10 36/9 R |
| 2011/0258885 | A1 | * | 10/2011 | Rutherford | A43B 3/00 36/136 |
| 2012/0030966 | A1 | * | 2/2012 | Huynh | A43B 3/108 36/11.5 |
| 2013/0014407 | A1 | * | 1/2013 | Savage | A43B 3/108 36/88 |

* cited by examiner

*Primary Examiner* — Clinton T Ostrup
*Assistant Examiner* — Cameron A Carter
(74) *Attorney, Agent, or Firm* — Patrick J. S. Inouye; Krista A. Wittman (57) ABSTRACT

A post-operative shoe and method for construction thereof is provided. The post-operative shoe includes an outsole having a substantially flat surface with a heel segment, a midfoot segment, and a forefoot portion surrounded by an outer edge. Each bore includes an open end on the outer edge of the forefoot portion and extending partially towards the heel segment. One or more flex rods each configured to fit within the bores and comprising a front end with threading corresponding to the threading of the bore are provided.

18 Claims, 10 Drawing Sheets

POST-OPERATIVE SHOE AND METHOD FOR CONSTRUCTION THEREOF

FIELD

The present invention relates in general to shoes and, in particular, to a post-operative and post-trauma shoe and method for construction thereof.

BACKGROUND

Patients recovering from foot surgery are often required to wear bandages to cover the incision and prevent swelling. The bandages make wearing regular shoes difficult and foot surgery patients often have a specialized shoe for wearing post-operation, which is large enough to expand and accommodate the foot as well as the bandage around the foot. Additionally, post-operative shoes protect and support the foot after surgery. Additionally, these shoes may be required for use in patients suffering foot trauma or injury that requires bandages or stabilization of the foot for an extended period of time.

Conventional shoes, such as by Darco International or AliMed, typically have a rigid sole with a shoe upper that includes a closed heel portion and an opening along the top of the foot through which the patient can insert his foot and bandage. The opening can be closed by multiple hook and loop straps, usually two, which cross over the top of the foot and can be tightened to apply pressure and hold the foot securely. D-rings are often used to allow the user to easily tighten and secure the straps. However, if the straps are too tightly adjusted, constriction occurs at the site of the straps, which are pressed into the user's foot, causing additional swelling and potentially increasing the recovery time. As well, the rigid outsole restricts the patient's normal gait, which is preferred immediately after surgery; however, this continued restriction can hinder the recovery process as time passes.

A normal gait involves movement and bending of the foot over multiple phases, including, for example, heel strike to flat foot, flat foot through mid-stance, mid-stance through heel off, and heel off to toe off. Allowing the patient to slowly return to his normal gait is beneficial to the recovery process because the wound or incision site can be milked to pull fluid out of the foot and prevent swelling. The normal movement of the foot during walking helps alleviate fluid build up around the wound, reducing post-operation swelling and improving the recovery time.

Accordingly, a shoe that provides adjustable flexibility as a patient recovers after surgery is needed to decrease recovery time. Preferably, the shoe will allow the user to eventually walk with a normal gait as the recovery process progresses and can provide a seamless transition back to their normal footwear.

SUMMARY

Immediately after surgery, a patient's foot should be supported and protected, which is often performed using a combination of bandages and a support shoe. Current support shoes used after surgery generally have a rigid outsole to prevent the foot from moving and causing opening of the incision site, such as by ripping of the skin or sutures, if any. However, as time passes and the foot begins to heal, allowing the user to return to his normal gait can decrease the recovery time. However, conventional shoes prevent users from walking with a normal gait due to the rigid outsole. A post-operative shoe that allows for variable flexibility in the outsole to accommodate a patient throughout the recovery process can speed the time needed for recovery by allowing the patient to gradually return to his normal gait.

An embodiment provides a post-operative shoe and method for construction thereof. The post-operative shoe includes an outsole having a substantially flat surface with a heel segment, a midfoot segment, and a forefoot portion surrounded by an outer edge. Each bore includes an open end on the outer edge of the forefoot portion and extending partially towards the heel segment. One or more flex rods each configured to fit within the bores and comprising a front end with threading corresponding to the threading of the bore are provided.

Still other embodiments will become readily apparent to those skilled in the art from the following detailed description, wherein are described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Conventional shoes used by patients after foot surgery provide protection and support to the foot that underwent surgery in an attempt to decrease the healing time. However, current designs can unintentionally prolong a patient's recovery time by preventing the patient from returning to his normal gait while wearing the post-operative (post-op) shoe and allowing swelling to occur, such as due to excessive tightening of the shoe straps. A post-op shoe with removable flex rods, such as flex rods, in the outsole can allow for adjustment of flexibility based on an amount of time passed since the patient's surgery and the patient's speed of recovery.

Figure 1:
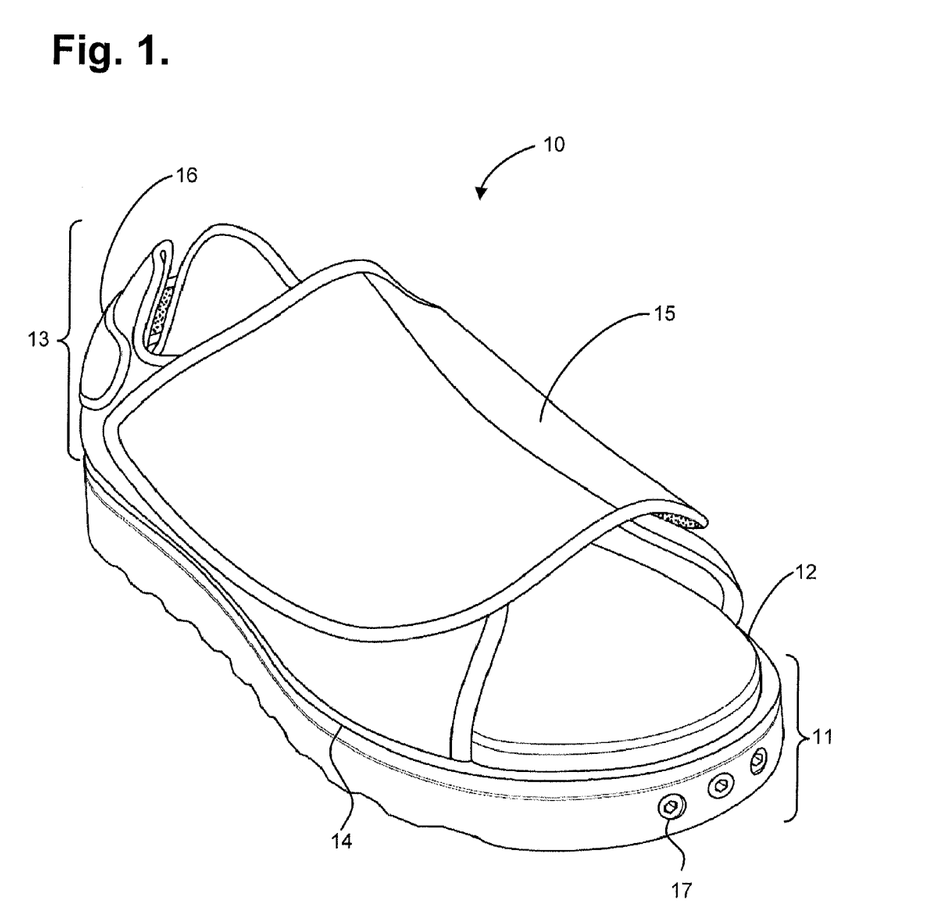
FIG. 1 is a perspective view of a post-operative shoe, in accordance with one embodiment.

The post-op shoe provides flexibility by including one or more removable flex rods that can be inserted into an outsole. FIG. 1 is a perspective view of a post-operative shoe 10, in accordance with one embodiment. The post-op shoe includes an outsole 11, an insole 12, and an upper portion 13, which includes side supports 14, a top compression panel 15, and a heel strap 16. The outsole has a substantially flat top surface with rounded toe and heel ends. In one embodiment, the toe end includes a larger rounded end than the heel end. The bottom of the outsole can include grooves that extend within a portion of the outsole and that correspond with tread. The outsole can be symmetrically designed along a plane of a foot to accommodate both left and right feet. However, in a further embodiment, the outsole can be specifically designed to separately fit a left foot and a right foot.

The outsole 11 can include a heel segment, a midfoot segment, and a forefoot segment. The heel segment is located on a proximal end of the outsole and the toe segment is located on a distal end. The midfoot segment is located between the heel and forefoot segments. Specifically, the heel segment can run from a proximal end of a user's heel to a distal end of the arch, while the midfoot segment covers the arch, and the forefoot segment runs from a distal end of the midfoot segment to the user's toes.

One or more bores 17 can be formed within a distal end of the outsole 11, at the toe end, and can run along a length of the foot. Specifically, each bore 17 has an opening formed within an outer surface of the outsole at the distal end of the forefoot segment and can extend to the proximal end of the forefoot segment or a distal end of the midfoot segment. However, the bore can be longer or shorter in further embodiments. The bores can be configured to accept flex rods (not shown) of variable rigidity to increase or decrease flexibility of the shoe. Ideally, the post-op shoe should be most rigid immediately after surgery to keep the foot from moving, but as time passes and the foot begins to recover, the flexibility of the shoe can be increased to allow the user to gradually return to his normal gait. The bores and flex rods are further discussed below with reference to FIGS. 7-10B.

The insole 12 can be located directly above the top surface of the outsole or above a top surface of a midsole (not shown) or outsole, and can be removable or permanently affixed. The insole 12 can sit in an outsole cavity designed to accommodate a varying foot bed thickness in the toe area. In one embodiment, the thickness of the foot bed can be 3-4 mm. However, other measures are possible. The insole 12 can be secured to the outsole with hook and loop tabs in the heel area and may also include a hook and loop tab in the toe area. In one embodiment, a shape of the insole 12 can be the same as the outsole, but slightly smaller so that an edge is formed around the outer top surface of the outsole. The insole 12 helps absorb shock to the foot upon movement by the user, provides appropriate arch support and can be made from ethylene vinyl acetate or polyurethane; however, other materials are possible. A sock liner of the insole 12 can include antibacterial and antifungal properties that help inhibit infection in the foot.

The upper portion 13 of the post-op shoe is affixed to the outsole 11 and extends over and around the users foot to hold the shoe 10 on the foot. The upper portion 13 includes the side supports 14, top compression panel 15, and heel strap 16. Specifically, the side supports 14 can be affixed to the outsole 11 or secured between the insole 12 and the outsole 11. Additionally, the side supports 14 can be affixed or secured using glue or other fastening material. In one embodiment, the side supports 14 are made from a single piece of material, while in a further embodiment, the right side support and the left side support are constructed from different pieces of material.

The upper portion 13 can be made from a variety of materials, including fabric, neoprene, mesh, leather, or vinyl, as well as other types of material. In one embodiment, neoprene or other flexible material, such as mesh, is used. Silver nanoparticles can be incorporated into the lining material of the upper portion of the shoe, including the side supports 14, top strap 15, and heel strap 16. The silver nanoparticles have antibacterial and antifungal properties that help inhibit infection in the foot. Additionally, the post-op shoe can be washable to allow a user to clean the shoe and prevent infection.

Figure 2:
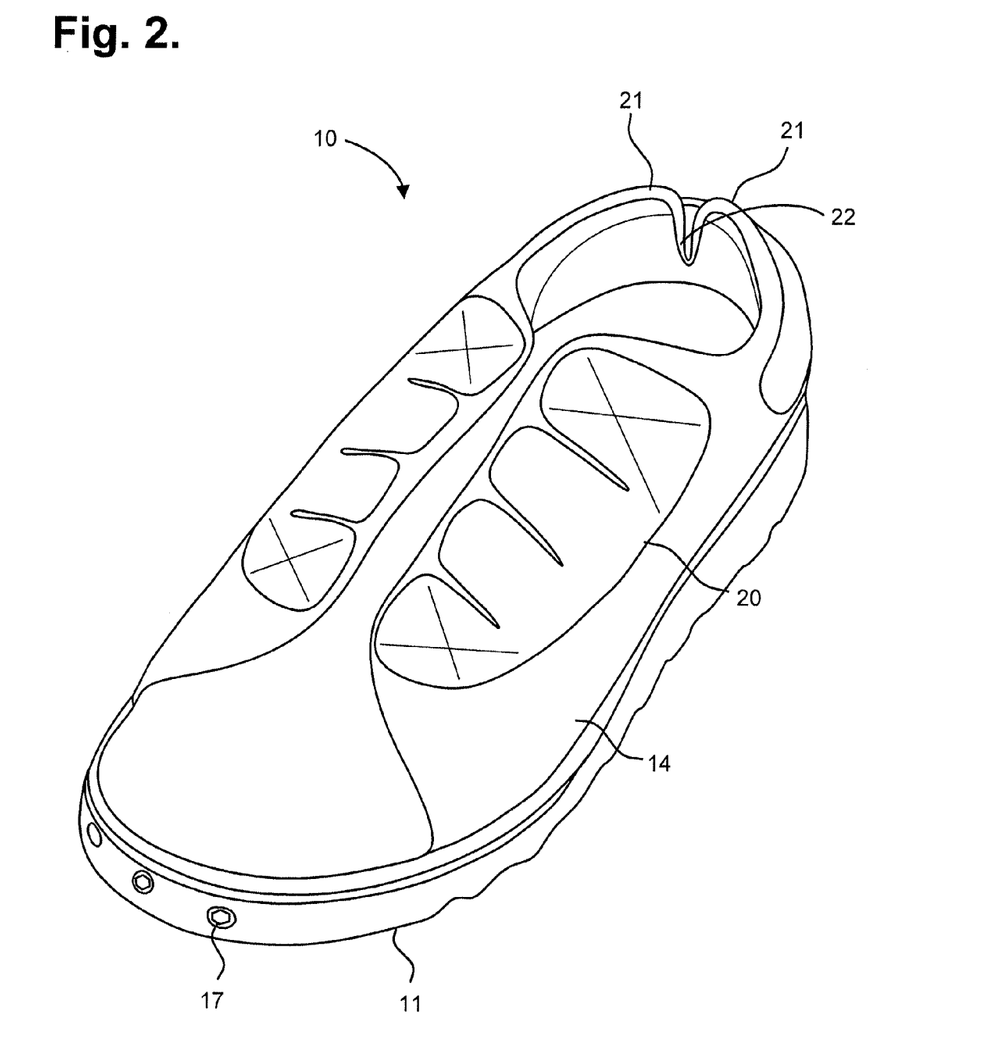
FIG. 2 is a top view of the post-operative shoe of FIG. 1 without a top compression panel.

A user can easily insert his foot, including any bandages, into the post-op shoe via openings at the top of the shoe and at the back of the shoe, which can be covered using the top compression panel and heel strap respectively. FIG. 2 is a top view of the post-operative shoe of FIG. 1 without the top compression panel. The side supports 14 are affixed on a bottom edge to the outsole 11 and are configured to fit comfortably around the sides of the user's foot. The left and right side supports 14 can extend along a length of the foot from the heel to just below the toes, so that the toes are exposed. As well, the side supports can extend over a top portion of the user's foot to create two top flap segments.

Fasteners 20 can be affixed to each of the top flap segments of the left and right side supports. The fasteners 20 can be affixed to the top surface of the side supports using thread, glue, or hook and loop fasteners. Other methods for affixing the fasteners are possible. The two top flap segments of the side supports can be connected by affixing the top compression panel 15 to the fasteners 20. In one example, the fasteners 20 can include hook material on the top surface, while the top compression panel 15 includes loop material on a bottom surface that faces the fastener 20 and connects to the hook material. Depending on a size of the user's foot, the top segments of the left and right side supports may not meet, but rather form an open passage between the two top sides above a top surface of the foot when in a closed position with the top compression panel affixed. However, for users with smaller feet, the two top flap segments can meet or overlap when in a closed position with the top compression panel affixed such that no gap exists. Affixing the top compression panel to the post-op shoe is further discussed below with reference to FIG. 3.

In the back of the shoe on a heel end, a slit 22 is formed between the left and right side supports. The slit 22 extends from a top of the side supports partially down to the outsole so that flaps 21 are formed on the left and right back ends of the side support 14. The openings in the back and on top of the shoe allow the user to fully pull down the left and right side supports to insert his foot. Once inserted, the user can pull the side supports up and around his foot.

Figure 3:
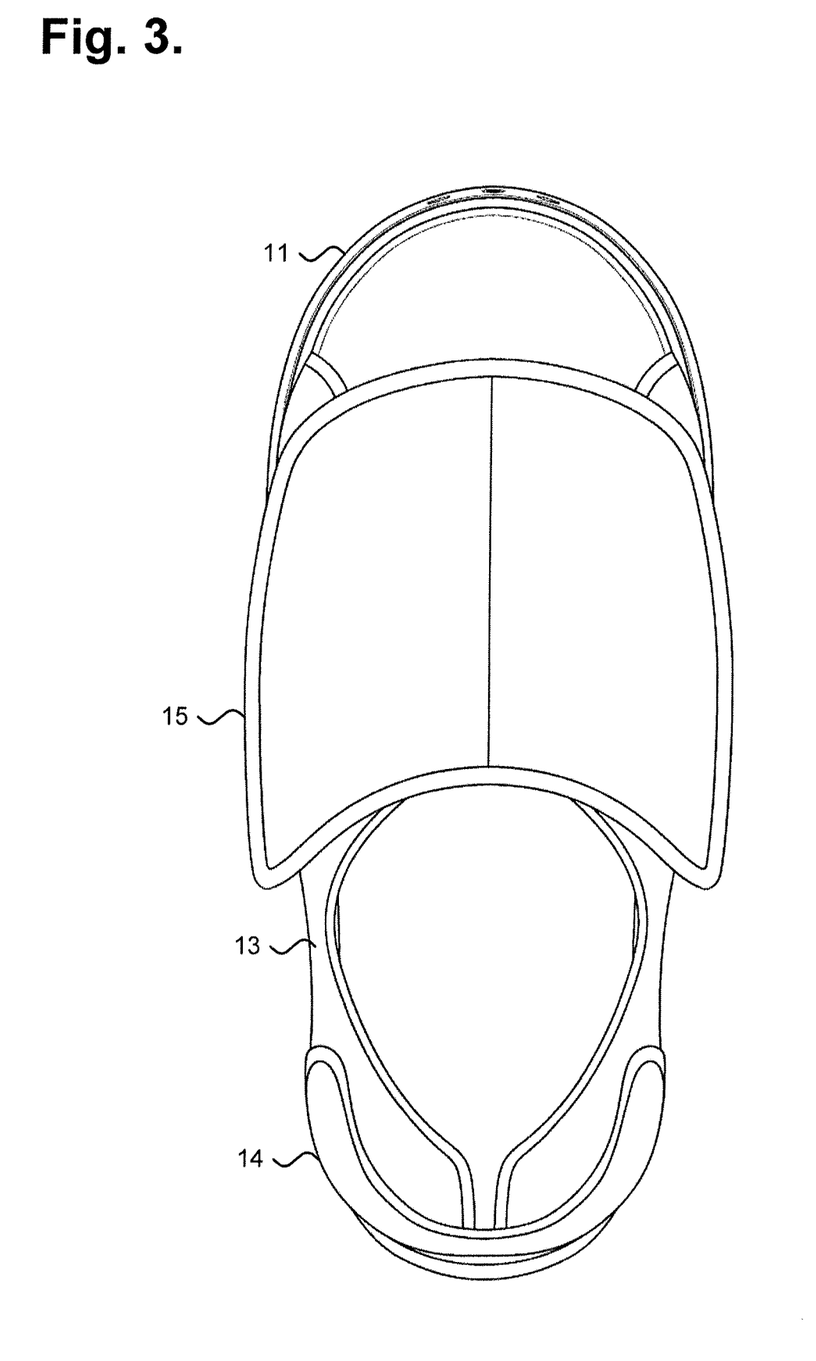
FIG. 3 is a top view of the post-operative shoe of FIG. 1.

The user can secure his foot in the post-op shoe by affixing the top compression panel and heel strap. FIG. 3 is a top view of the post-operative shoe of FIG. 1. The top compression panel 15 can be removably affixed to the top flap segments of the side supports to connect the two sides of the side supports in a closed position and prevent the user's foot from coming out of the shoe. The top compression panel 15 can be directly affixed to a top surface of the side supports or can be affixed via strap fasteners, as described above with respect to FIG. 2, by pressing the top compression panel onto the top flap segments of the side supports.

Figure 4:
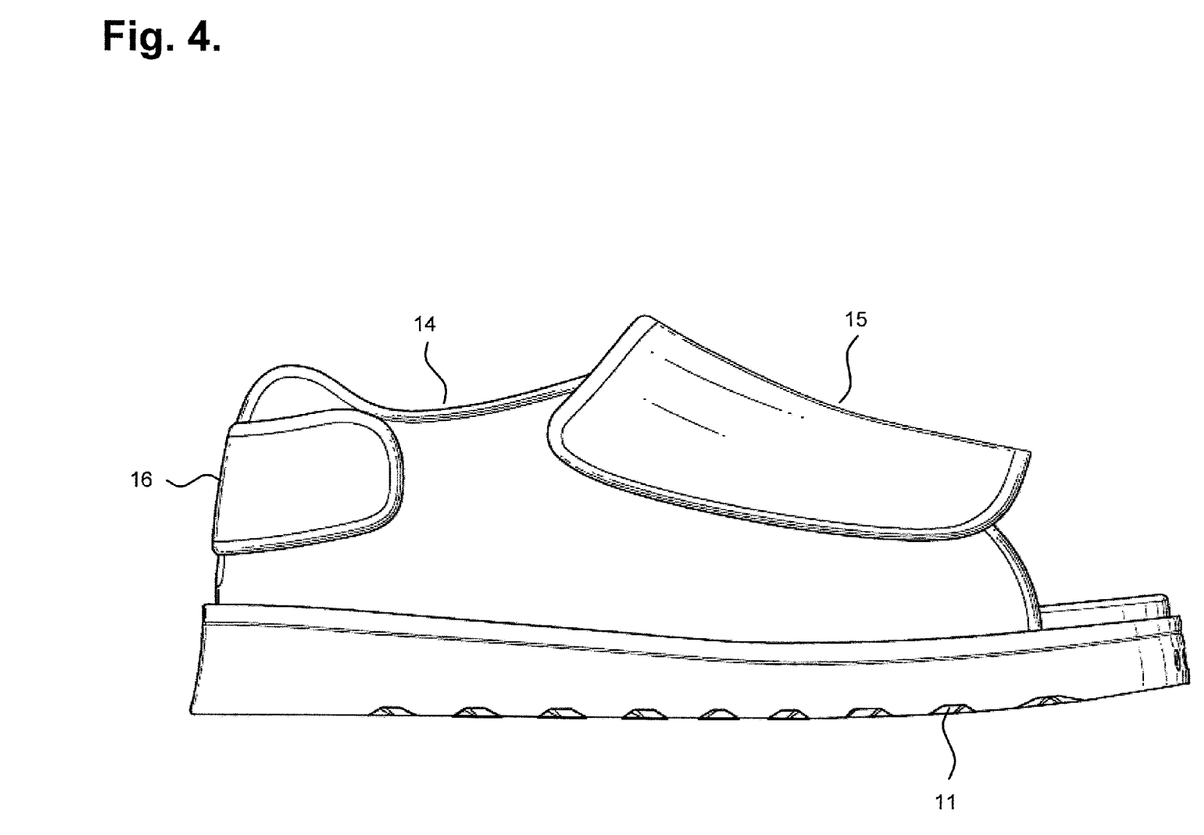
FIG. 4 is a side view of the post-operative shoe of FIG. 1.

The top compression panel can extend across the top flap segments of the side supports all the way to the outsole or only a portion of the way to the outsole. FIG. 4 is a side view of the post-operative shoe of FIG. 1. In this example, the top compression panel is affixed to the top flap segments and extends partially towards the bottom of the post-op shoe. The smaller a user's foot, the more the top compression panel overlaps the side supports.

Figure 5:
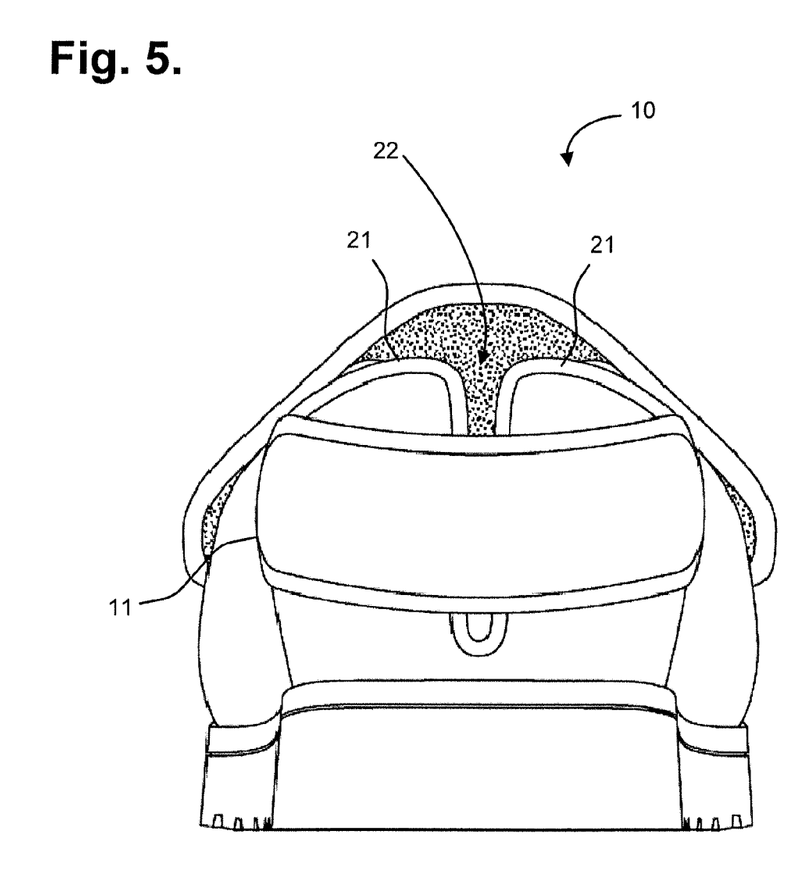
FIG. 5 is a back view of the post-operative shoe of FIG. 1.

In addition to the top compression panel, the heel strap can help secure the user's foot within the post-op shoe. Specifically, the heel strap 16 can be removably affixed to the side supports at the back of the post-op shoe to bring together the two heel flaps of the support sides and secure the user's heel from slipping out of the shoe. FIG. 5 is a back view of the post-operative shoe of FIG. 1. The two back flaps 21 of the side supports at the heel end are connected at a bottom segment closest to the outsole and a slot 22 is formed above the bottom segment where the flaps are connected and extends to the heel flaps of the side supports. The slot runs along the Achilles tendon of the user's foot so that the back flaps can fold down and the user can easily insert his foot into the shoe. The user can then close the back flaps to secure his foot by removably affixing the heel strap 16 to the side supports of the post-op shoe. Specifically, the heel strap can be placed perpendicularly over the slot 22 and fastening ends of the heel strap to the left and right flaps 21. The heel strap 16 brings together the two sides of the side support based on a size of the user's heel. In one embodiment, the two back flaps can overlap when the heel strap is affixed, such as when the user's heel is small. However, users with larger heels can adjust the heel strap so that the two back flaps remain untouching.

The heel strap 16 can be directly affixed to the flaps of the side supports or alternatively, can be affixed to strap fasteners (not shown). Whether directly affixed to the side supports or affixed via strap fasteners, various removable fastening methods can be used including, hook and loop, removable glue, or adhesive, as well as other fastening methods. In one example, an outer surface of the heel flaps of the side supports or the fasteners, if any, can include hook material, while a bottom surface of the heel strap 16, that faces the outer surface of the heel straps, can have loop material to fasten to the side support or fasteners, if any. Alternatively, the side supports or fasteners can have loop material and the heel strap 16 can have hook material.

Figure 6A:
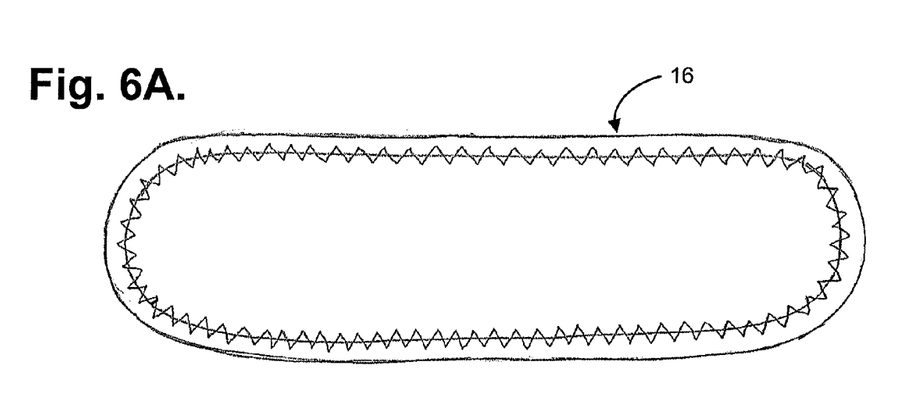
FIG. 6A is a top view showing, by way of example, a heel strap.

The heel strap, top compression panel, and fasteners help the post-op shoe adjust flexibility to the user's needs during the recovery period. FIG. 6A is a top view showing, by way of example, a heel strap. The heel strap 16 can have the shape of a rectangle, a rectangle with rounded ends, rectellipse, ellipse, or oval. Other shapes are possible. At a minimum, the heel strap should be long enough to affix to a first heel flap on a first side of the side support, extend over the slit, and affix at the opposite end to a second flap on the other side of side support. In one embodiment, a height of the heel strap should not exceed the height of the flaps or the side supports, which may cause discomfort to the user. The height of the side supports at the heel end can be measured from a top surface of the outsole at which the side supports are partially affixed up to a top edge of the side supports that are positioned near the user's Achilles tendon.

The heel strap 16 can be made from the same material as the side supports or from different material. In one embodiment, the heel strap 16 should be flexible so that when the user walks, the heel strap expands slightly to allow movement of the user's foot, while preventing the user's heel from slipping out of the shoe at the same time.

Figure 6B:
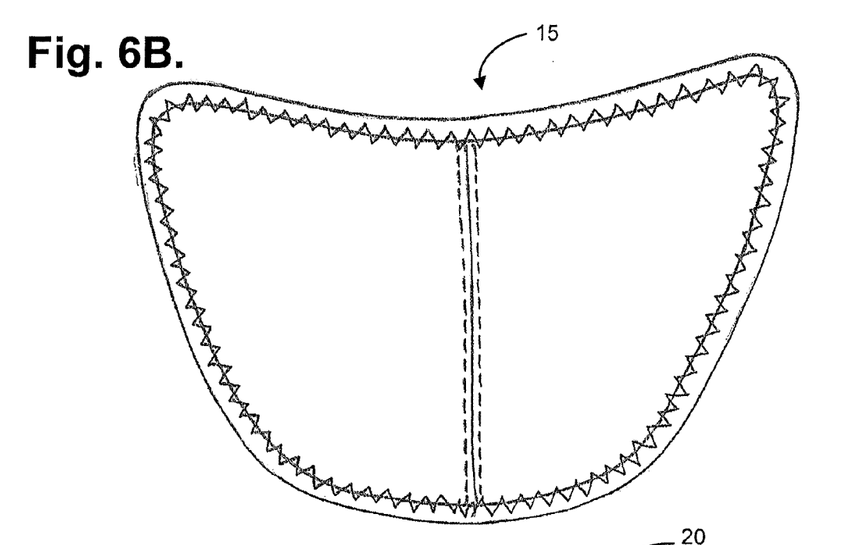
FIG. 6B is a top view showing, by way of example, a top compression panel.

The top compression panel can also be made out of the same material or different material from the side supports and heel strap. FIG. 6B is a top view showing, by way of example, a top compression panel 15. The top compression panel 15 can have a rectangular, square, rectellipse, ellipse, or oval shape. At a minimum, the top compression panel should be large enough to adequately cover the top portion of the user's foot, excluding the toes. In one embodiment, the top compression panel should run along a top of the user's foot from a point near where the foot meets the leg to a point just before the toes. As well, the top compression panel should be wide enough to attach to a top flap segment of a first side support on one end, cover any existing channel, and attach on the other end to the opposite top flap segment. A single top compression panel prevents swelling of the foot that can be caused by multiple thinner straps such as those located on conventional shoes used after surgery, which tend to constrict blood flow and create additional swelling and/or fluid buildup.

Figure 6C:
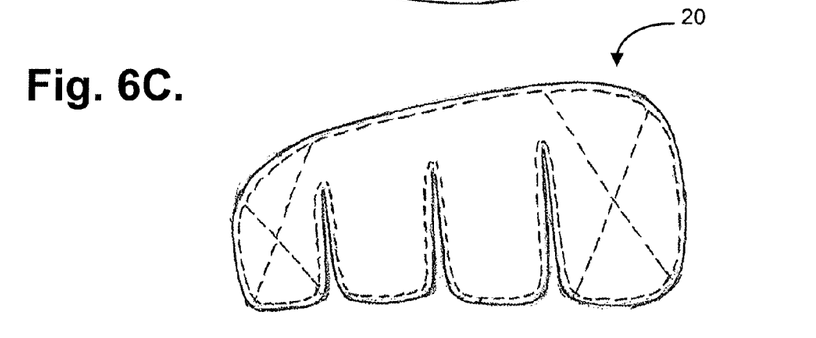
FIG. 6C is a top view showing, by way of example, a strap fastener.

The top compression panel can be directly affixed to the top segment of the side supports or alternatively, can be affixed to the side supports via fasteners. FIG. 6C is a top view showing, by way of example, a strap fastener 20. The strap fastener can have a rectangular shape, a rectangular shape with arms, or the shape of a letter E or F. The rectangular shape with arms can include a straight edge along which two or more arms protrude on the opposite side, similar to the letters E and F. Other shapes are possible as well. The arms allow the top flap segment of the side supports to move under the strap fastener so that when the top compression panel is affixed to the fasteners, the upper shoe portion is able to adjust as the user moves his foot, such as when walking.

A strap fastener can be permanently or removably affixed to each top flap segment of the side supports using thread, glue, adhesive, or hook and loop material. Other methods for affixing the strap fastener to the side supports are possible. Specifically, the top straps can be affixed to the top segments such that the straight edge is positioned away from the channel with the arms extending towards the edge of the top segment at the passage. The strap fastener can also be used to removably affix the heel strap to the back of the side supports.

The upper portion of the post-op shoe should be moveable to allow a user to easily put on the shoe despite any bandages and should also be flexible to move comfortably with the user, while supporting and protecting the user's foot. In contrast, the outsole of the shoe should constrict any movement of the user's foot immediately after surgery to prevent reopening of an incision site or tearing of the skin or sutures. However, as the user recovers, increased movement of the foot is encouraged so that the user can return to his normal gait while walking. Thus, gradual flexibility of the outsole is desired to allow normal movement of the user's foot.

Figure 7:
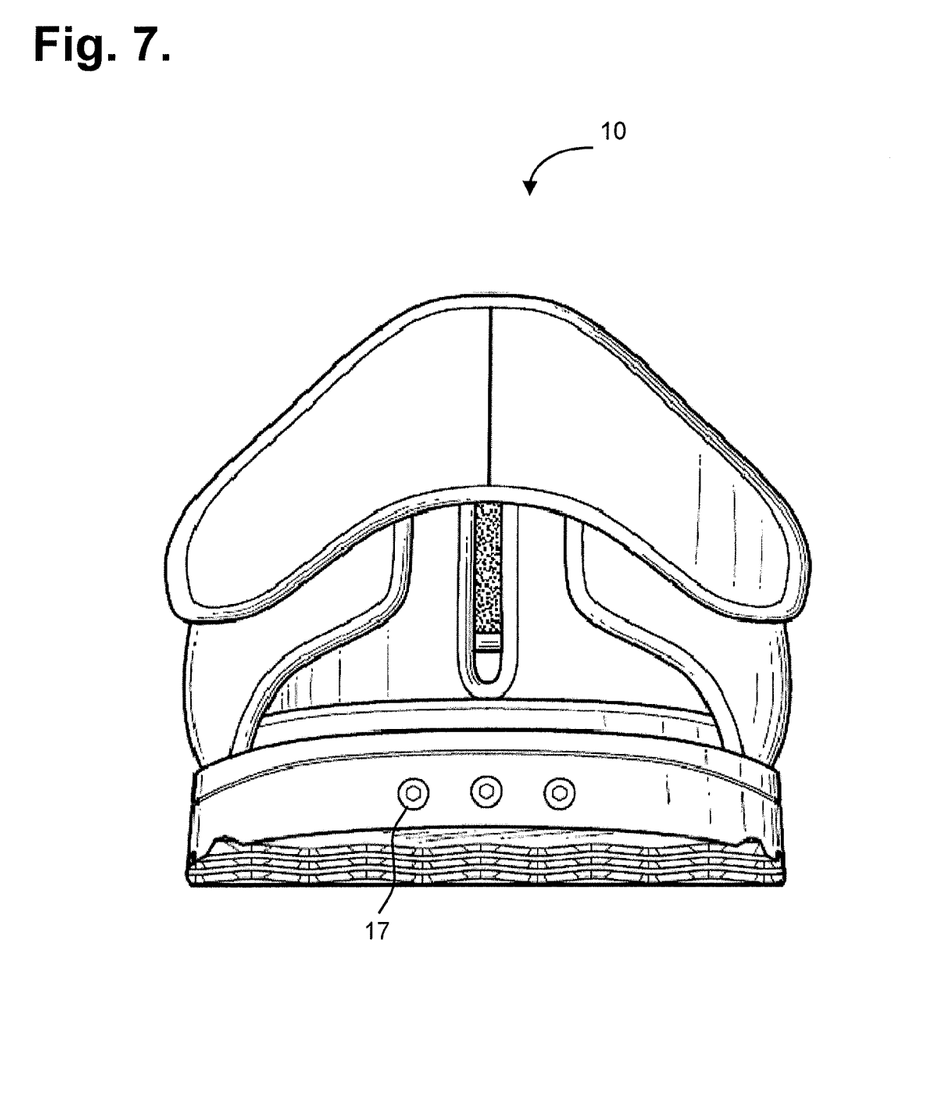
FIG. 7 is a front view of the post-operative shoe of FIG. 1.

To increase the flexibility of the outsole, flex rods of varying rigidity can be inserted. FIG. 7 is a front view of the post-operative shoe 10 of FIG. 1. One or more bores 17 are formed within a front of the outsole 11, such that openings to the bore are located on an outer surface of the front of the outsole, specifically, at the distal end of the forefoot segment. The bores can be circular, square, or triangular. Other shapes are possible. The shape of the bore is configured to conformably surround a flex rod, which can be inserted into the bore through the opening.

Figure 8A:
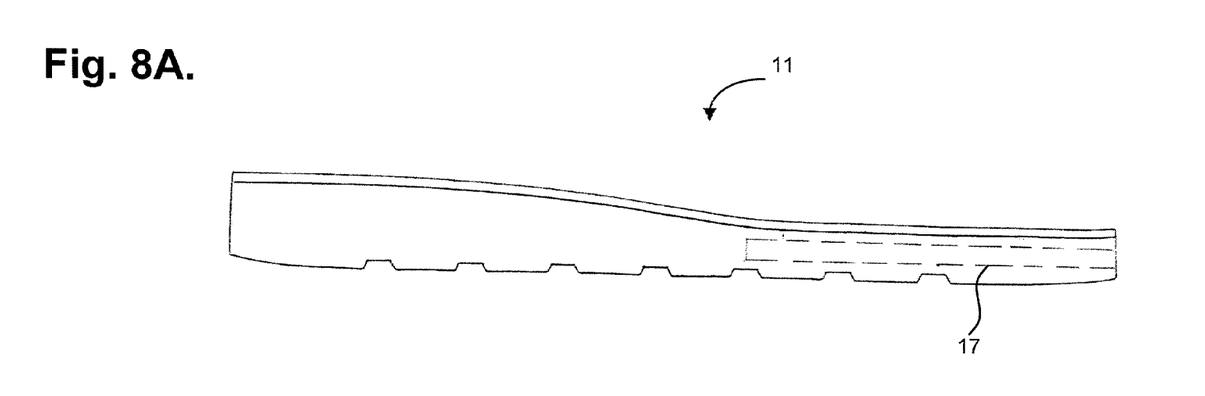
FIG. 8A is a side view of an outsole for the post-operative shoe of FIG. 1.

The bore extends within the middle of the outsole. FIG. 8A is a side view of the outsole 11 of the post-operative shoe in FIG. 1. The bores 17 can extend within the outsole from the opening on a front of the outsole at the distal end of the forefoot segment to a proximal end of the forefoot segment. However, in further embodiments, the bores can extend past the forefoot segment into the midfoot or heel segments or can be shortened to extend only partially through the forefoot segment. Within the bore, immediately past the opening, an inner surface can be threaded. For example, the threading can be consistent with an internal thread, commonly known as a female side, which interconnects with corresponding external threading on the flex rods, known as a male side. The screw thread secures the flex rods within the bores and prevents the bores from falling out of the outsole.

Figure 8B:
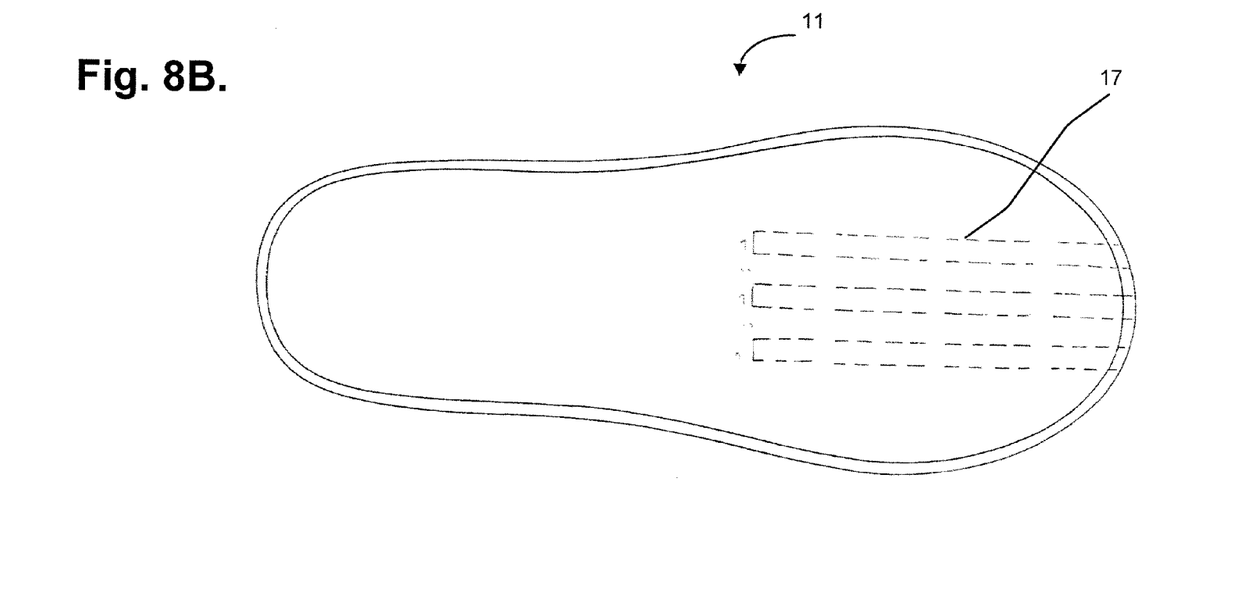
FIG. 8B is a top view of the outsole of FIG. 8A.

A number of bores located within the outsole can depend on a size of the post-op shoe. For instance, larger post-op shoes may have more bores than smaller post-op shoes. Alternatively, the same number of bores can be used for different shoe sizes. FIG. 8B is a side view showing, by way of example, the outsole 11 of FIG. 8A. The bores 17 can be evenly spaced from one another along the front surface of the outsole 11 at the distal end of the forefoot segment. Specifically, the middle bore is located along a center point on a front of the forefoot segment of the outsole. The other two bores 17 are located at equal distances, one to the left and one to the right of the middle bore.

However, as described above, other numbers of bores are possible. When an even number of bores are provided, the bores may be evenly spaced from a center of the front surface of the outsole at the distal end of the forefoot segment, rather than inserting a bore at the center point, such as when there are an uneven number of bores. The distance between the bores can be predetermined, based on a width of the user's foot or based on a number of bores to be formed. Other methods for determining placement of the bores are possible.

Figures 9A, 9B:
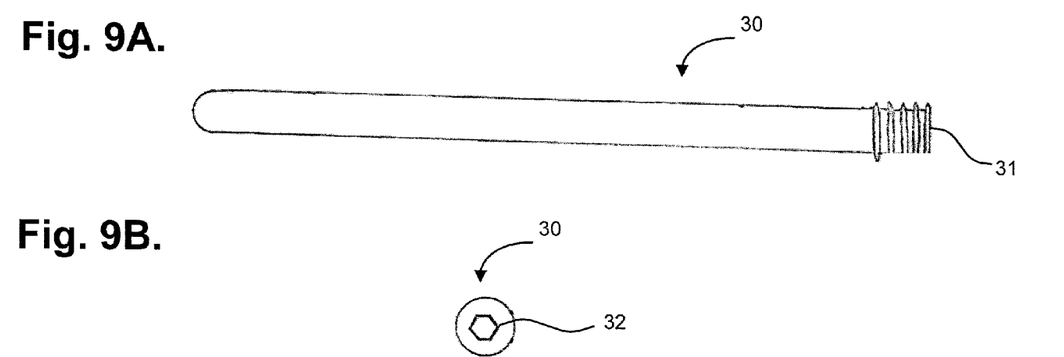
FIG. 9A is a side view of a flex rod for use with the post-operative shoe of FIG. 1.
FIG. 9B is a front view of the flex rod of FIG. 9B.

Each of the bores can be the same shape and size or can have different shapes and sizes. At a minimum, the bores must be configured to receive at least one flex rod. FIG. 9A is a side view of a flex rod 30 for inserting into outsole of FIGS. 8A and 8B. The flex rods 30 can be made from polyvinyl chloride, polyphosphoester urethane or foam, and can have a cylindrical, rectangular, rectangular prism, or cuboid shape. Other types of materials and shapes are possible. In one embodiment, the flex rods 30 can have a rounded proximal end that is inserted into the bore and a portion of the opposite end can be threaded 31 on an outer surface to screw into the internal threading of the bore to secure the flex rod.

A screw head can cover the threaded end of the flex rod. FIG. 9B is a front view of the flex rod 30 of FIG. 9B. The screw head 32 can have a pan, dome, round, mushroom, flat, or oval shape, as well as other shapes. The outer surface of the screw head 32 can include a notch for inserting a screwdriver to screw the support member into the bore. In one embodiment, the screw head has a diameter that is larger than the opening of the bore, while in a further embodiment, the screw head can fit within the bore.

A user can insert a flex rod 30 into a bore by placing the rounded end of the bore into the opening of the bore on the outer surface of the outsole. The flex rod will slide in until the opposite end with threading reaches the internal threading of the bore. At this point, a screwdriver can be used to rotate the flex rod through the internal threading of the bore. In one embodiment, a Phillips screwdriver is used to insert the support member. Other screwdrivers are possible and should match the notch in the screw head of the support member.

Figure 10A:
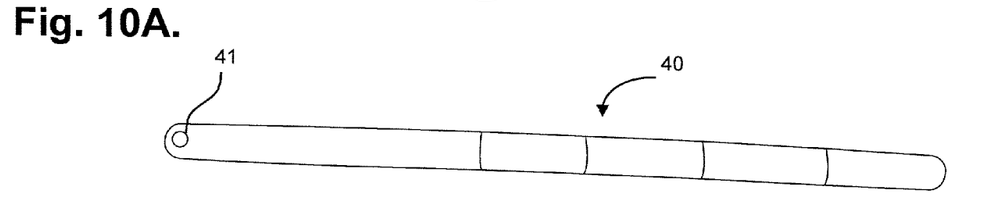
FIG. 10A is a side view of an alternative flex rod for use with the post-operative shoe of FIG. 1.

Alternately, the flex rods can have a hole in the distal end that can be extracted with an instrument. FIG. 10A is a side view of an alternative flex rod for use with the post-operative shoe of FIG. 1. A hole can be formed within a proximal end of the flex rod, which is nearest the outer surface of the outsole when inserted in the bore. The flex rod 40 can slide into the bore until the entire flex rod is inserted.

Figure 10B:
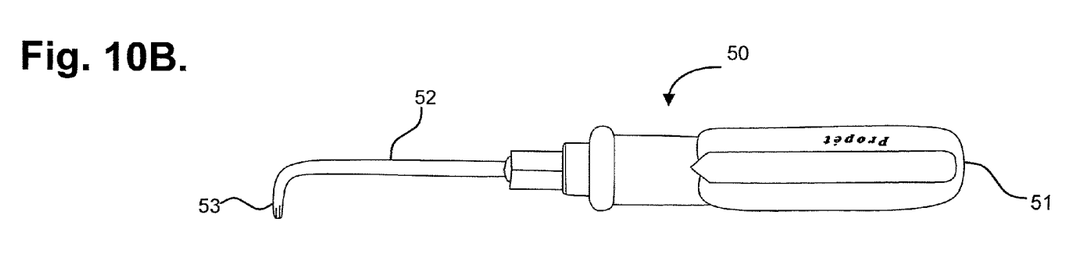
FIG. 10B is a side view of an instrument for inserting and removing the alternative flex rod of FIG. 10A from the post-operative shoe of FIG. 1.

To remove the flex rod 40, a user can utilize a small tool or other instrument with a hook for inserting into the hole and pulling out the flex rod. FIG. 10B is a side view of an instrument for inserting and removing the alternative flex rod of FIG. 10A from the post-operative shoe of FIG. 1. The instrument can include a screwdriver or hook tool, as well as other types of instruments. At a minimum, the instrument should be able to be inserted into the hole of the flex rod to move the flex rod into or out of the bores. The hook tool shown in FIG. 10B can include a handle 51, body 52 and hook 53. The hook 53 is inserted into the hole of the flex rod and a user pulls on the instrument handle to pull the flex rod out of the bore. Conversely, the user can use the instrument to insert the flex rod in the bore. In a further embodiment, the flex rods may include grooves along their length in order to release the vacuum that can be created as the flex rods are inserted.

The flex rods can have varying rigidity to allow the outsole to become more or less flexible. In one embodiment, three sets of three flex rods can be provided and color-coded to identify the rigidity of the flex rods. Flex rods with the color code, red, can be the stiffest, while, yellow coded flex rods are less rigid, and green coded flex rods are the most flexible. Other numbers of flex rods and colors are possible. Additionally, the outsole can be worn without any flex rods to obtain a maximum flexibility.

The flex rods inserted into the post-ops shoe can have the same rigidity or different levels of rigidity. For example, if a user needs more support on the left side of his foot, he can insert a red flex rod in a bore located on the left side of the outsole and yellow or green flex rods in the remaining bores. Other combinations of flex rods are possible.

Figure 11:
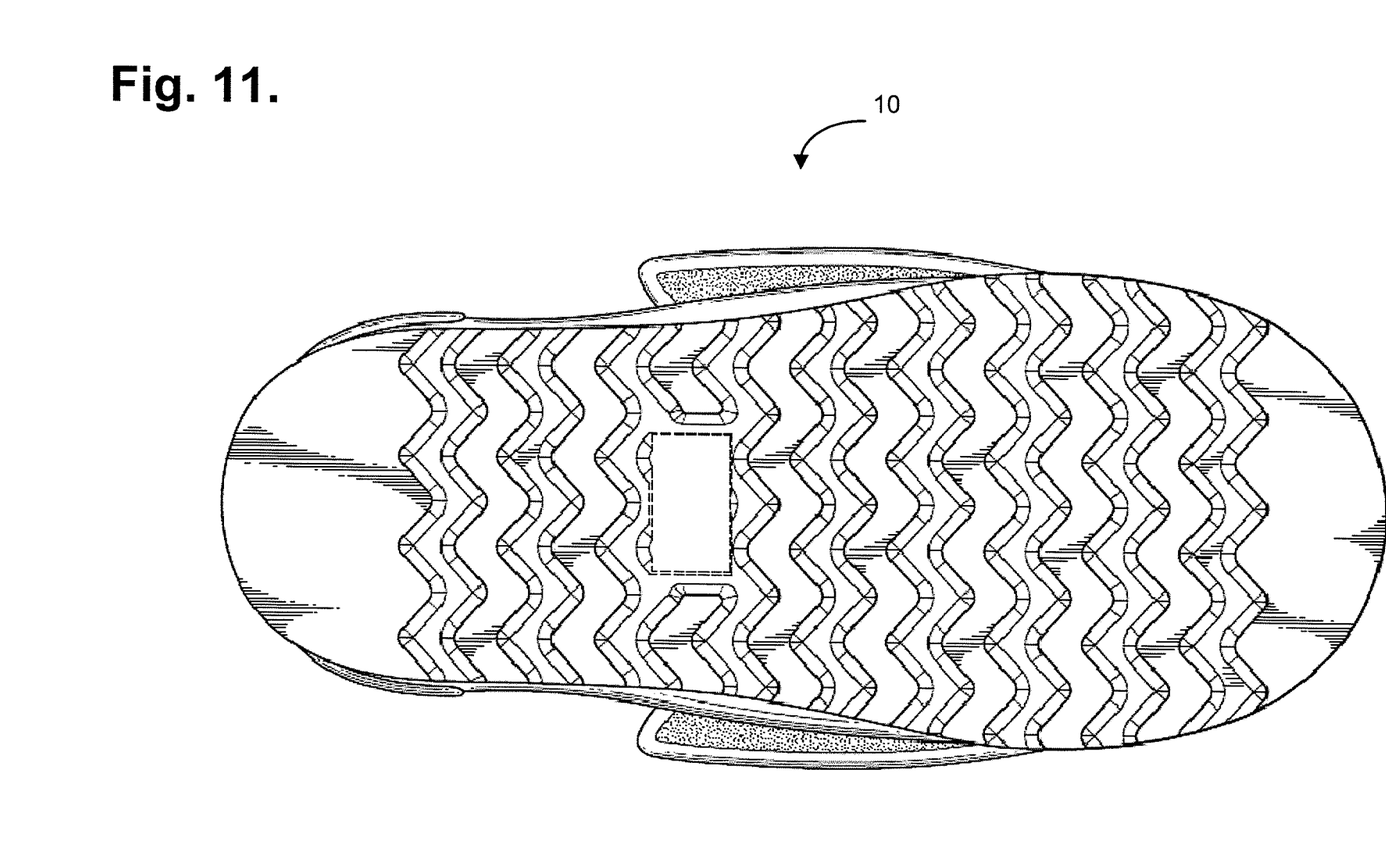
FIG. 11 is a bottom view of the post-operative shoe of FIG. 1.

In one embodiment, the bottom of the post-op shoe can include tread to prevent the user from slipping while wearing the shoe. FIG. 11 is a bottom view of the post-operative shoe of FIG. 1. The bottom of the outsole can have a wave pattern with raised ridges and concave valleys. However, other types of tread are possible.

If any portion of the post-op shoe is uncomfortable, the user can adjust the top compression panel, heel strap, and flex rods. Each of the top compression panel and heel strap can be removed by pulling each away from the side supports. Once removed, the top compression panel or heel strap can be repositioned on the side supports to connect the top flaps or the heel flaps respectively. The flex rods can be interchanged with other flex rods of different rigidity by removing the flex rods located in the bores, such as by screwing out the members or removing with a hook tool, and subsequently, replacing the removed flex rods with different flex rods.

While the invention has been particularly shown and described as referenced to the embodiments thereof, those skilled in the art will understand that the foregoing and other changes in form and detail may be made therein without departing from the spirit and scope of the invention.

What is claimed is:
1. A post-operative shoe, comprising:
an outsole having a substantially flat surface surrounded by an outer edge, and the outsole further comprising a plurality of evenly spaced bores each having an open end on the outer edge of a forefoot portion of the outsole and extending in a longitudinal direction from the forefoot portion and terminating at a midpoint of the outsole; and
a first flex rod having a first rigidity, a second flex rod having a second rigidity, and a third flex rod having a third rigidity, wherein each of the flex rods has a different rigidity from the other flex rods, and are configured to fit within at least one of the bores, the flex rods comprising a front end with threading that extends only over a portion of the flex rods and corresponds to threading of that bore.

2. A post-operative shoe according to claim 1, further comprising:
   side supports affixed to an inner surface of the outsole and configured to conformably surround a user's foot.

3. A post-operative shoe according to claim 2, further comprising:
   a heel strap removably affixed to a back side of at least one of the side supports at a heel end of the outsole.

4. A post-operative shoe according to claim 2, further comprising:
   a top compression panel configured to adjustably affix across a top segment of the side support over a top of the user's foot.

5. A post-operative shoe according to claim 1, further comprising:
   a screw top affixed to the front end of each flex rod.

6. A post-operative shoe according to claim 5, wherein the screw tops of the flex rods are each configured to accept a screwdriver.

7. A post-operative shoe according to claim 1, further comprising:
   two or more sets of the flex rods, each set comprising at least two flex rods having a common rigidity, wherein each set of flex rods has varying rigidity.

8. A post-operative shoe according to claim 1, further comprising:
   an insole affixed to a top surface of the outsole.

9. A post-operative shoe according to claim 8, further comprising:
   an antibacterial and antifungal liner covering at least a portion of the insole.

10. A post-operative shoe according to claim 1, wherein the bores and flex rods each comprise one of a circular, square, rectangular, and triangular shape.

11. A method for constructing a post-operative shoe, comprising:
   forming a plurality of bores evenly spaced within an outsole having a substantially flat surface surrounded by an outer edge, wherein the bored each have an open end on the outer edge of a forefoot portion of the outsole and extends in a longitudinal direction from the forefoot portion and terminates at a midpoint of the outsole; and
   providing a first flex rod having a first rigidity, a second flex rod having a second rigidity, and a third flex rod having a third rigidity, wherein each of the flex rods has a different rigidity from the other flex rods, and are configured to fit within at least one of the bores, the flex rods comprising a front end with threading that extends only over a portion of the flex rods and corresponds to threading of that bore.

12. A method according to claim 11, further comprising:
   affixing side supports to an inner surface of the outsole and configured to conformably surround a user's foot.

13. A method according to claim 12, further comprising:
   providing at least one of a heel strap and a top compression panel with the outsole.

14. A method according to claim 11, further comprising:
   affixing a screw top to the front end of each flex rod.

15. A method according to claim 11, further comprising:
   providing one or more sets of the flex rods, each set comprising at least two flex rods having a common rigidity, wherein each set of flex rods has varying rigidity.

16. A method according to claim 11, further comprising:
   affixing an insole to a top surface of the outsole.

17. A method according to claim 16, further comprising:
   covering at least a portion of the insole with an antibacterial and antifungal liner.

18. A method according to claim 11, wherein the bores and flex rods each comprise one of a circular, square, rectangular, and triangular shape.

* * * * *